(12) United States Patent
Barreras, Sr. et al.

(10) Patent No.: US 6,192,279 B1
(45) Date of Patent: Feb. 20, 2001

(54) NON-INVASIVELY MANEUVERABLE LEAD SYSTEM

(75) Inventors: Francisco Jose Barreras, Sr., Miami; Oscar Jimenez, Coral Gables, both of FL (US)

(73) Assignee: Medtronic, Inc., Minneapolis, MN (US)

( * ) Notice: Under 35 U.S.C. 154(b), the term of this patent shall be extended for 0 days.

(21) Appl. No.: 09/255,957

(22) Filed: Feb. 23, 1999

(51) Int. Cl.$^7$ .................................................. A61N 1/05
(52) U.S. Cl. ................................. 607/117; 607/116
(58) Field of Search ......................... 607/46, 61, 2, 607/63, 116, 117; 600/372, 373, 393

(56) References Cited

U.S. PATENT DOCUMENTS

| | | | |
|---|---|---|---|
| 3,598,128 | * 8/1971 | Chardack | 607/27 |
| 3,822,708 | * 7/1974 | Zilber | 607/46 |
| 5,674,274 | * 10/1997 | Morgan et al. | 607/123 |
| 5,762,599 | * 6/1998 | Sohn | 600/30 |
| 5,895,416 | * 4/1999 | Barreras, Sr. et al. | 607/62 |

* cited by examiner

*Primary Examiner*—Kennedy Schaetzle
(74) *Attorney, Agent, or Firm*—Thomas R. Vigil

(57) ABSTRACT

The method and system for non-invasively repositioning at least one stimulating electrode on a lead relative to tissue, such as nerve tissue, in a body includes elements for carrying out the method and the steps of: providing a lead having at least one stimulating electrode thereon which is located skew to an elongate axis of the lead; implanting the lead in a body; implanting in the body a drive mechanism having structure for engaging and rotating the lead; and, providing an exterior signal generating and transmitting mechanism for transmitting electromagnetic signals from outside the body to the drive mechanism implanted in the body for causing the drive mechanism to rotate the lead thereby to adjust the position of the at least one stimulating electrode on the lead relative to tissue in the body.

25 Claims, 6 Drawing Sheets

NON-INVASIVELY MANEUVERABLE LEAD SYSTEM

BACKGROUND OF THE INVENTION

1. Field of the Invention

The present invention relates to a method and system or apparatus for non-invasively adjusting the position of at least one implanted electrode.

2. Description of the Prior Art

Heretofore, leads designed for electrical stimulation of human tissue generally comprise electrodes at their distal end which are connected to contacts at their proximal end via insulated conductor wires threaded inside a non-conductive sheath. In general, stimulation leads are used to transport electrical pulses from an implanted pulse generator to the target tissue.

In the case of spinal cord stimulation, the target tissue is a secluded nerve fiber(s) within the spinal cord which transport a distinct neurological message to or from the brain. Two examples of a neurological message are (1) a signal to the brain intended to trigger a defensive or protective action, such as pain or (2) a signal from the brain intended to contract a specific muscle, such as the urinary bladder sphincter.

In the first example, electrical stimulation can be used to modify the pain signal in order to induce analgesia by activation of the endogenous opiate pain suppression system in a specific part of the body.

In the second example, electrical stimulation can be used to cause the contraction of the sphincter in the urinary bladder in order to prevent urinary incontinence.

Trying to recruit specific nerve fibers without affecting other nerve fibers can be a very difficult and time consuming medical procedure. When using electrical stimulation for pain control, a trial stimulation is applied to the spinal cord using an external pulse generator, with the goal of positioning the electrode so that a fine, tingling sensation called paresthesia, is felt in the entire area where there is pain. During this trial stimulation, a patient needs to be fully awake in order to report to the physician when optimal localization of the electrode has taken place. Once the optimal electrode position is achieved, the lead is sutured in place, disconnected from the external pulse generator and connected to an implantable, permanent pulse generator which is then programmed to the same stimulation values as the external one.

Some types of neural stimulation are notoriously ineffective, such as lower back stimulation. The spacing between electrodes and the length of each electrode become very critical factors for effective lower back stimulation. For some patients the physician may choose a lead having large spacing between electrodes in order to achieve complete paresthesia coverage, only to find out that such large spacing makes it too difficult if not impossible to recruit the target nerve. A lead having closely spaced electrodes may facilitate recruitment of the target nerve but may not provide complete paresthesia coverage. The main problem here is that manual pushing or pulling of the implanted lead by the physician often results in larger than desired changes in electrode position, making location of the "sweet spot" (paresthesia location) extremely difficult. An electromechanical means for micro-stepping (rotating) the electrode position, such as described hereinafter, will allow the physician to locate the desired location quicker and with less effort, improving the chances for successful therapy.

Furthermore, one of the major obstacles in preventing long term success of spinal cord stimulation for some patients, has been electrode displacement from their originally implanted position relative to the target nerve. Electrode displacement in most cases is due to normal flexing of the spinal column as the patient goes about his/her normal daily activities. What appears to occur is that the lead retracts slightly when the patient bends forward, but does not fully recoil back to its original location upon the patient returning to the up-right position. This results in a decreased or total loss of medical therapy. In this case, if the system of the present invention is used and the patient is provided with an electrode position controller, a physician or a properly trained patient may be able to non-invasively reposition the electrode to the original site and avert an expensive and uncomfortable surgical procedure to manually reposition the electrode.

SUMMARY OF THE INVENTION

It is the objective of the present invention to provide a completely implanted neurological system which is capable of non-invasively changing the location of the stimulating electrodes in relation to the target nerve.

There are three parts to the lead system of the present invention, namely, (1) an Electrode Position Controller used by the physician to non-invasively command implanted spiral electrodes to change their position in relation to the stationary target nerve within the spinal cord, (2) a Lead Extension which connects a Stimulating Lead to the pulse generator, and (3) the Stimulating Lead having one or more skew or spiral electrodes at its distal end.

The Lead Extension comprises at its proximal end, (1) one or more contact rings for making electrical connection to the pulse generator, (2) one or more insulated wires to carry the electrical pulses from the pulse generator to the stimulating lead, and (3) at its distal end, one or more canted coils to make electrical contact with the contact rings in the Stimulating Lead, a micro-motor, a reduction gear, a shaft and controlling circuitry.

The Stimulating Lead comprises at its proximal end, (1) a mandrel which locks into the shaft of the micro-motor in the Lead Extension, and one or more metal rings to make electrical connection with the canted coils in the Lead Extension, (2) one or more insulated wires to carry the electrical pulses from the Lead Extension, and (3) one or more insulated wires to carry the electrical pulses from the Lead Extension, and (4) at its distal end, one or more Spiral Electrodes.

The Electrode Position Controller sends electromagnetic waves which are picked up and rectified into direct current pulses by the electronic circuit within the Lead Extension. These current pulses are applied to the micro-motor which causes its gear shaft to rotate just a few degrees per burst of electromagnetic waves. Since the Stimulating Lead is locked to the gear output shaft, the Stimulating Lead will also rotate when the micro-motor is energized. As the Stimulating Lead is rotated, the skew or spiral electrodes will slide perpendicularly to the target nerve, effectively changing, in very small and controlled steps, the position of the electrodes in relation to the target nerve.

DESCRIPTION OF THE PREFERRED EMBODIMENT(S)

Figure 1:
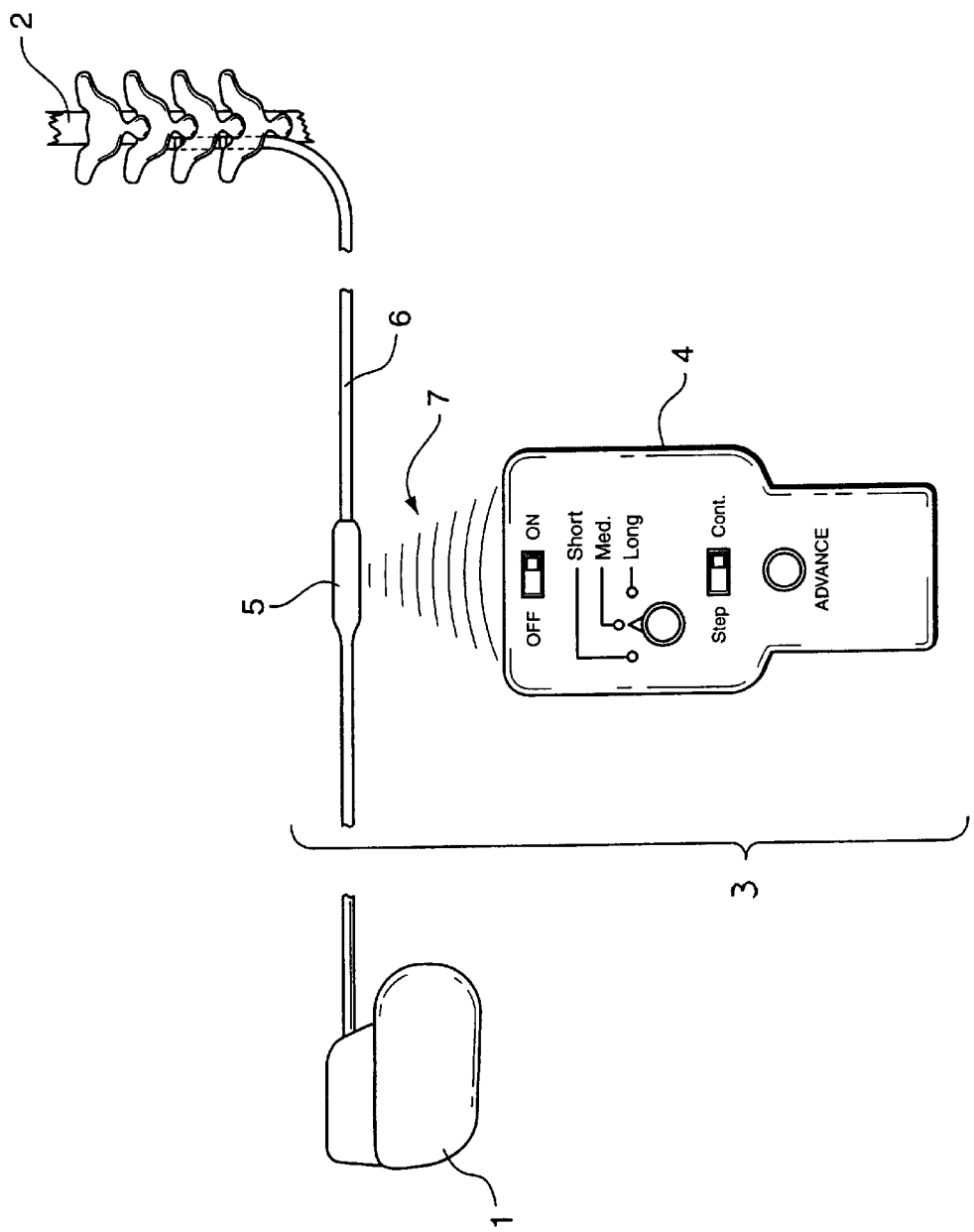
FIG. 1 is a block electrical schematic circuit diagram of the Non-Invasively Maneuverable Lead System constructed and operable according to the teachings of the present invention for non-invasively changing the position of the electrodes in relation to the targeted nerve within the spinal cord. The Lead System illustrated is used in conjunction with an implanted pulse generator to deliver stimulation pulses to the spinal cord.

In FIG. 1 there is illustrated a block diagram of a non-invasively maneuverable lead system 3 constructed according to the teachings of the present invention and connected between an implanted pulse generator 1 and a spinal cord 2.

An electrode position controller 4 of the system 3 is used by a physician or medical technician to cause non-invasive, longitudinal micro-steps in lead position within the epidural space proximal to the spinal cord 2. This is accomplished by transmitting electromagnetic waves (drive signals) from the electrode position controller 4 to the lead extension 5 which causes small, controlled changes in electrode position of a stimulating lead 6 relative to the stationary target nerve.

Figure 2:
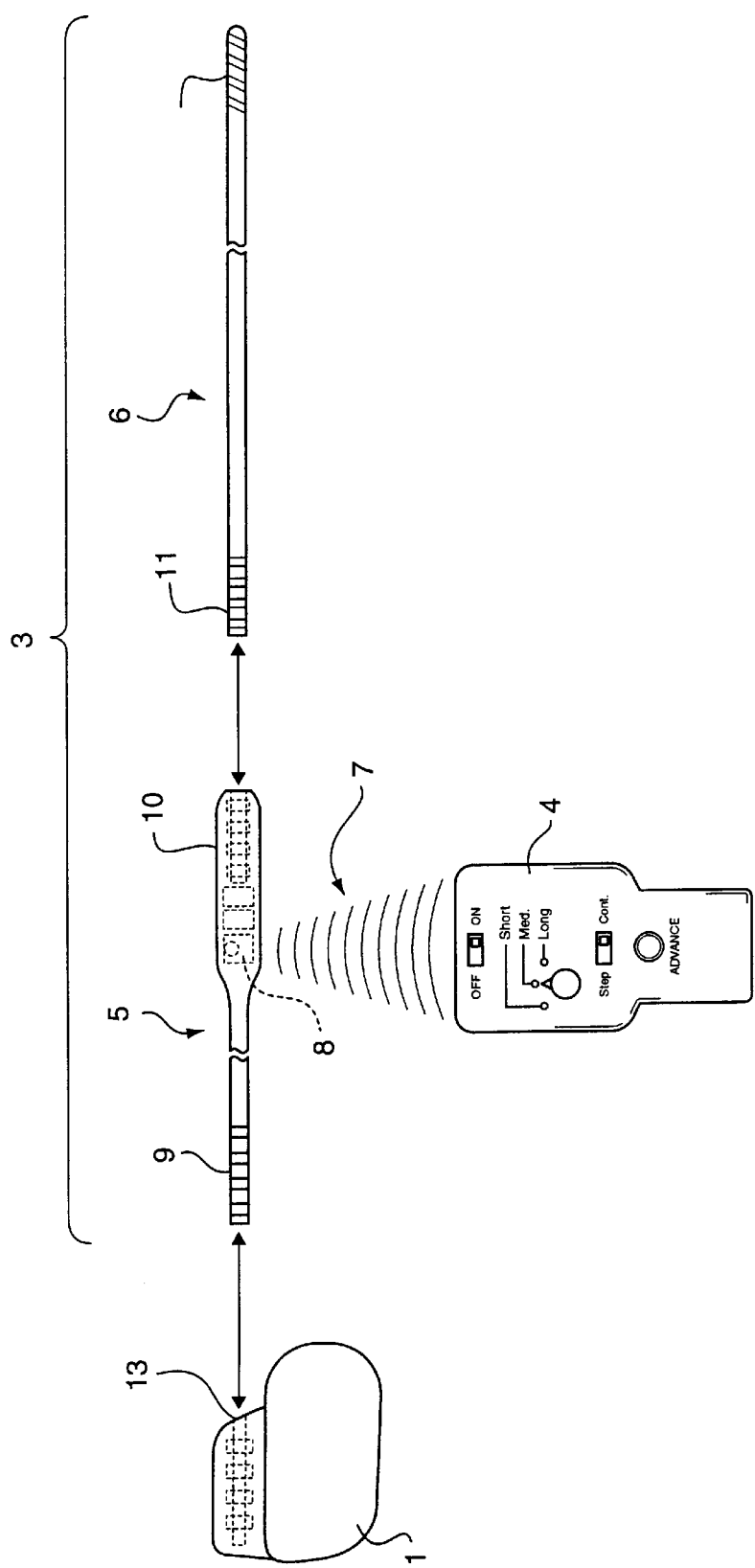
FIG. 2 is an exploded view of the Non-Invasively Maneuverable Lead System, showing the three major components of the system.

In FIG. 2 there is shown an exploded view of the non-invasively maneuverable lead system 3. It shows how an implanted pulse generator 1, the lead extension 5 and the stimulating lead 6 are connected. It also shows the electrode position controller 4 transmitting electromagnetic waves 7 to the microelectronic circuit 8 within the lead extension 5. Note that (1) a proximal end 9 of the lead extension 5 plugs into a receptacle 13 of the implanted pulse generator 1 and (2) a proximal end or proximal end portion 11 of the stimulating lead 6 plugs into a distal end 10 of the lead extension 5.

Figure 3A:
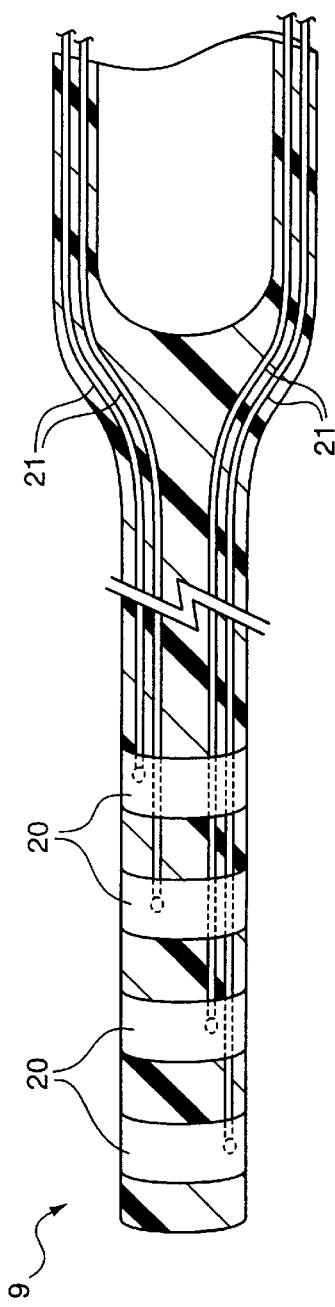
FIG. 3A is a longitudinal plan view, with portions broken away, of proximal end portions of the Lead Extension showing all the external and internal components, including the micro-motor, gear case and shaft.
Figure 3B:
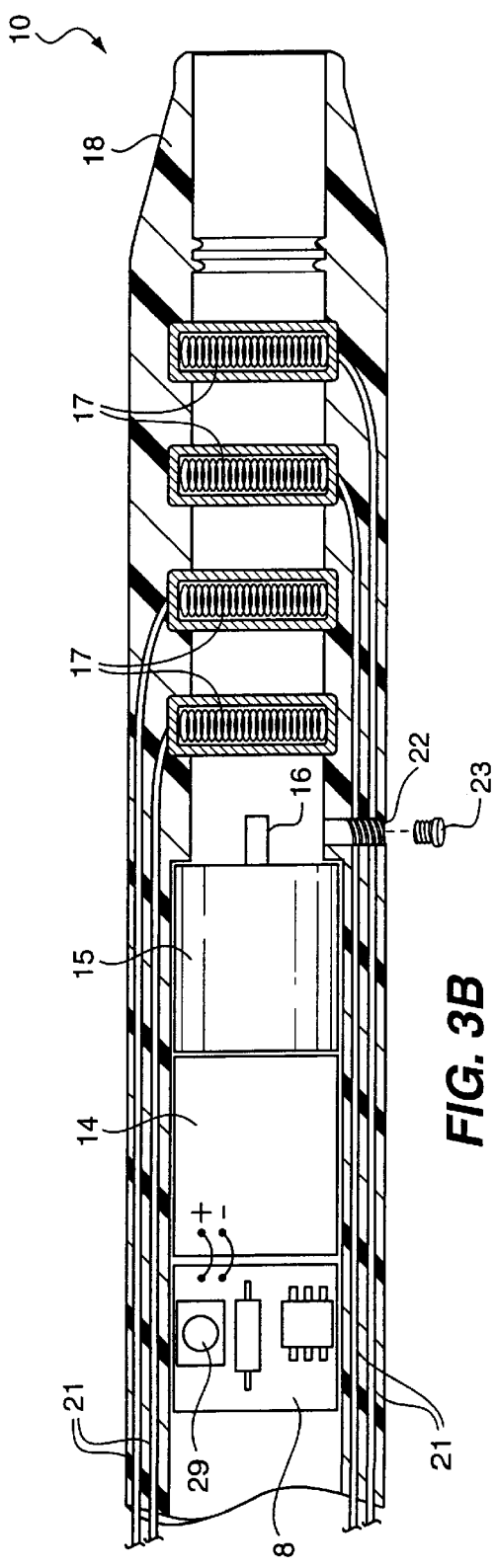
FIG. 3B is a longitudinal plan view, with portions broken away, of the distal end of the Lead Extension showing all the exterior and interior components, including the micromotor, gear case and shaft.
Figure 3C:
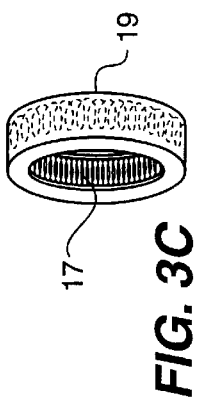
FIG. 3C is a perspective view of one of the garter spring-shaped toroidal coil electrodes.

In FIG. 3 there is illustrated the lead extension 5. The entire assembly is enclosed in a bio-compatible, leak-proof polymer 18 in order to provide long term performance. Looking at the distal end 10, the microelectronic circuit 8 picks up the electromagnetic waves 7 transmitted by the electrode position controller 4 (FIG. 1), and converts them into current pulses which are applied to a micro-motor 14. A gear case 15 reduces the RPM of the micro-motor 14 and increases the torque placed on an output shaft 16. Canted coils or a garter spring shaped coils 17 are used to maintain positive electrical contact with contact rings 26 (FIG. 4) of the stimulating lead 6 while it rotates. Note in the angular view, that the canted coils 17 are confined within a retainer 19 in order to prevent their displacement as the stimulating lead 6 is inserted.

Looking at the proximal end 9, lead extension contact rings 20 are utilized to make positive electrical connection to the contact blocks of the implanted pulse generator 1 (FIG. 1). This allows insulated wires 21 to carry the stimulation pulses to the canted coils 17 at the distal end 10 and to the stimulation lead 6.

Figure 4:
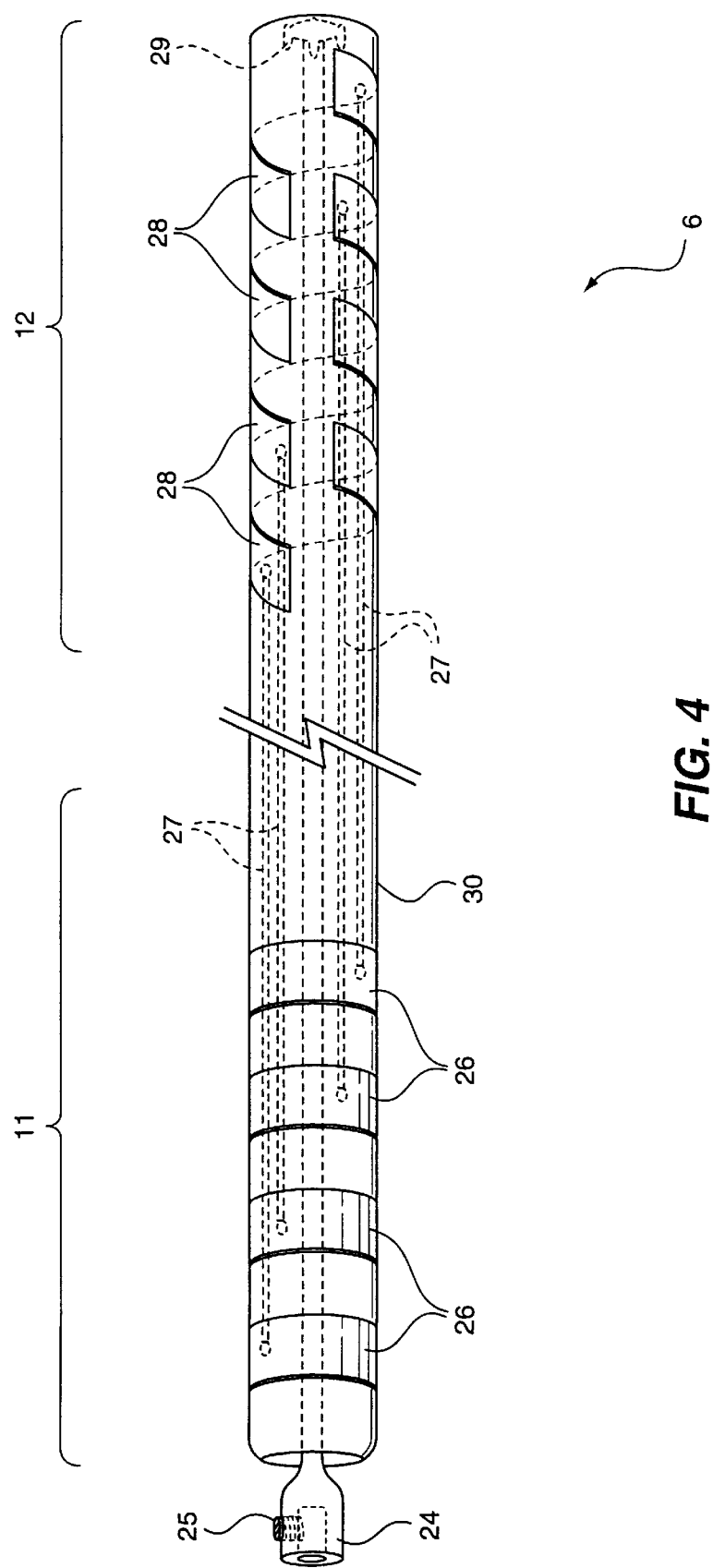
FIG. 4 is a longitudinal plan view of the Stimulating Lead, showing all the internal and external components. In this example, the Stimulating Lead is shown having four spiral electrodes at its distal end.

The microelectronic circuit 8 (FIG. 5) includes an inductor 29 which is used to pick up the electromagnetic waves 7 transmitted by electrode position controller 4. These pulses are converted into DC current pulses which drive micromotor 14. Micro-motor 14 drives reduction gear case 15 in order to provide the torque required to rotate stimulating lead 6. An access hole 22 is used to provide access to tighten a set screw 25 (FIG. 4). A plug 23 is used to seal the access hole 22.

In FIG. 4 there is shown the stimulation lead 6. A mandrel 24 is used to transfer the rotational motion of the output shaft 16 (FIG. 3) to a distal end or distal end portion 12 of the stimulation lead 6. The mandrel 24 includes a set screw 25 which is used to lock the mandrel 24 of the stimulation lead 6 to the output shaft 16 of the lead extension 5. The proximal end 11 of stimulation lead 6 includes the contact rings 26 which are used to make positive electrical contact with the canted coils 7 of the lead extension 5 (FIG. 3).

Insulated wires 27 then carry the stimulation pulses to skew or spiral electrodes 28 at the distal end 12 of the stimulation lead 6. An anchor 29 is used to cause the distal end 12 of the stimulation lead 6 to follow the turning motion at the mandrel 24 on a 1:1 ratio. An insulated sheath 30 prevents intrusion of body fluids into the stimulation lead 6. The skew or spiral electrodes 28 are surgically placed proximal to the target nerve in order to stimulate them. As the output shaft 16 turns, it also turns the stimulating lead 6. Since each electrode is spirally wound with a significant tilt for almost one full diameter of stimulating lead 6, as lead 6 slowly turns it causes the spiral electrodes 28 to effectively slide perpendicular in relation to the stationary target nerve.

Upon the stimulation lead 6 turning a full 360°, the electrodes will effectively return to their starting position. This simplifies the design by allowing the use of the micromotor 14 which only turns in one direction.

Figure 5:
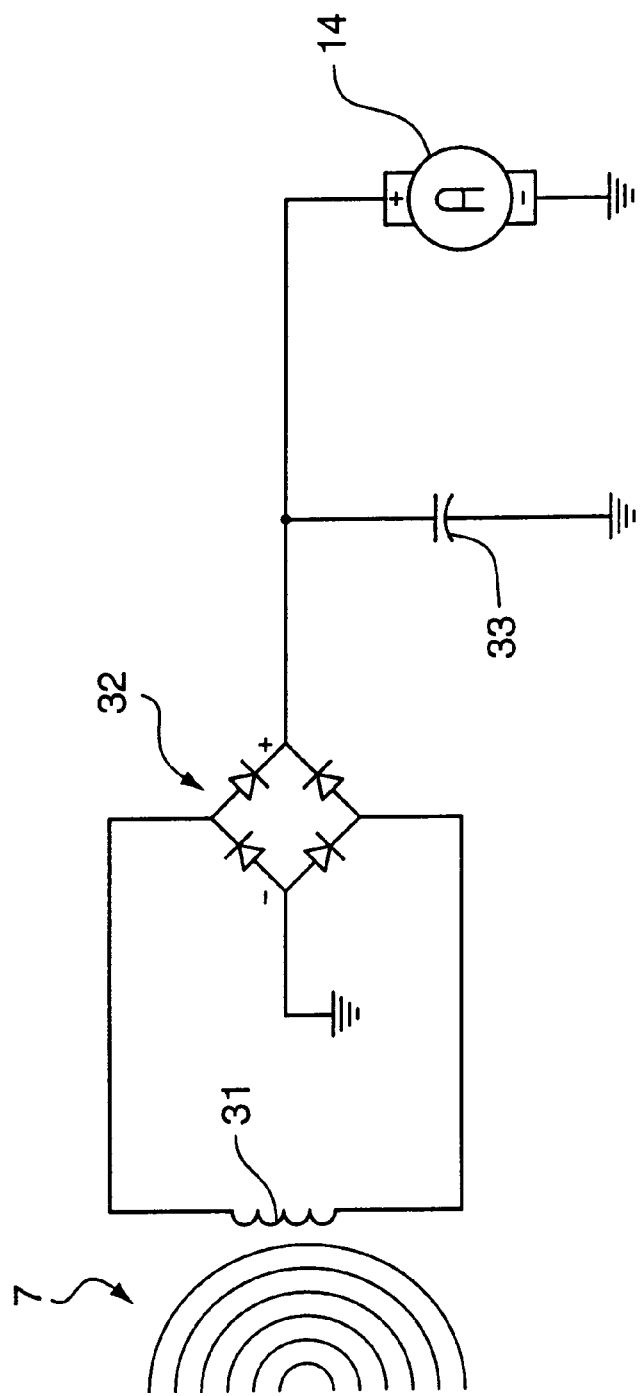
FIG. 5 is a block electrical schematic circuit diagram of the micro-electronic circuit within the Lead Extension used to capture the electromagnetic pulses transmitted by the Electrode Position controller (external to the human body).

In FIG. 5 there is shown a schematic electrical circuit diagram of the microelectronic circuit 8 incorporated into the lead extension 5 which is used to convert the electromagnetic waves 7 transmitted by the electrode position controller 4 from outside the human body into current pulses used to drive the micro-motor 14.

The microelectronic circuit 8 comprises an inductor 31, a bridge rectifier 32, and a capacitor 33 connected in the manner shown. Electromagnetic waves 7 are coupled into the inductor 31, rectified by the bridge rectifier 32 and the resulting electrical energy is stored into the capacitor 33. At this point, the micro-motor 14 draws current from the capacitor 33 and begins to turn. The duration of each burst of electromagnetic waves determines how many degrees the output shaft 16 (FIG. 3) will turn. If the gear case 15 has a slow gear ratio such as 256:1, burst duration can be adjusted to turn the output shaft 16 approximately 5° per burst. Since the spiral electrodes 28 are wrapped for a maximum of 320° of the lead diameter, if the spiral electrodes 28 (FIG. 4) are spaced 4 mm apart, each burst will cause the electrodes 28 to slide approximately 0.062 mm. This can be calculated using the following relationships:

$$(1) \text{ Number of steps per each revolution} = \frac{320°}{5°} = 64$$

$$(2) \text{ mm per step} = \frac{4 \text{ mm}}{72 \text{ steps}} = 0.062 \text{ mm}$$

Figure 6:
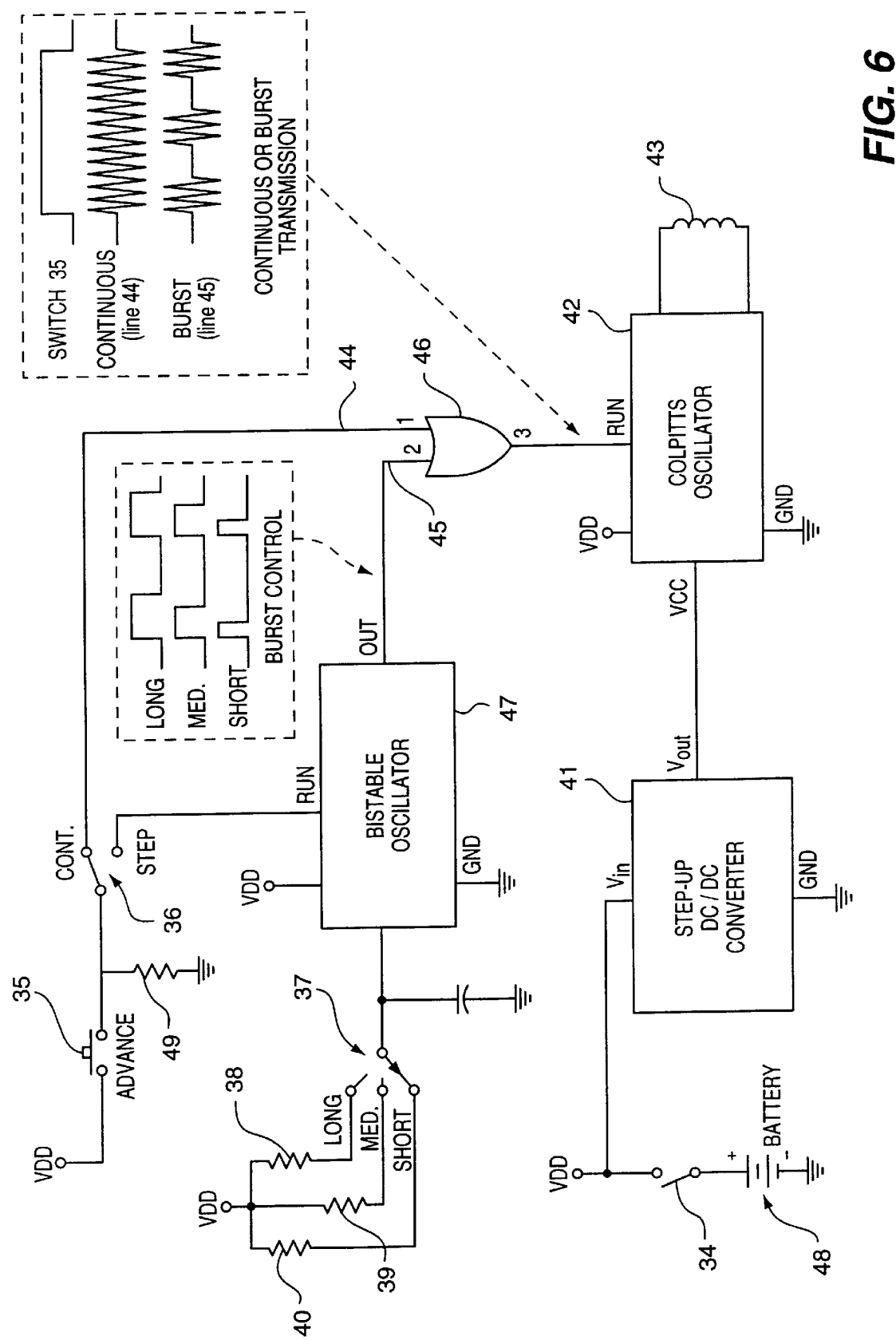
FIG. 6 is a block electrical schematic circuit diagram of the circuitry incorporated in the Electrode Position Controller and used to transmit the electromagnetic waves which control electrode position.

In FIG. 6 there is shown an electrical schematic circuit diagram of the circuitry included in the electrode position controller 4 which transmits the electromagnetic waves 7 in order to power the micro-motor 14. A switch 34 is used to turn a power supply (battery) on and off. A push button switch 35 is used to activate the transmission of electromagnetic waves while depressed. A switch 36 is used to select either "continuous" or "burst" displacement of the skew or spiral electrodes while switch 35 is depressed.

In the "continuous" mode the electromagnetic waves are transmitted continuously as long as switch 35 is held down and as shown in the waveform diagram portion of FIG. 6.

In the "burst" mode the electromagnetic waves are transmitted in bursts whose duration is controlled by the duty cycle of a bistable oscillator 47. A switch 37 is used to select short, medium or long electrode steps by controlling the duration of each burst of electromagnetic waves as explained above in connection with the description of FIG. 5 and as shown in the waveform diagram portion of FIG. 6.

A DC/DC converter 41 is used to increase the battery voltage to a higher value needed for adequate transmission power. A Colpitts oscillator 42 is used to generate the electromagnetic waves via an inductor 43. A bistable oscillator 47 is used to establish the duration (controlled by resistors 38, 39 or 40) and repetition rate of each burst of the electromagnetic waves.

When the switch 36 is set to the "continuous" mode, an input 44 of an OR gate 46 switches high while the switch 35 is held down, thus allowing the Colpitts oscillator 42 to continuously generate electromagnetic waves to cause the spiral electrodes to slide continuously.

When the switch 36 is set to the "burst" mode and the switch 35 is held down, an output 45 of the bistable oscillator 47 will alternatively switch high and low. The Colpitts oscillator 42 will generate electromagnetic waves only when output 45 is high but not while it is low, thus causing the spiral electrodes 28 (FIG. 4) to slide in very short steps.

We claim:

1. A method for non-invasively repositioning an electrode on a lead relative to nerve tissue in a body including the steps of:
  providing a lead having at least one stimulating electrode thereon which is located skew to an elongate axis of the lead;
  implanting the lead in a body;
  implanting in the body a drive mechanism having structure for engaging and rotating the lead; and,
  providing an exterior signal generating and transmitting mechanism for transmitting electromagnetic signals from outside the body to the drive mechanism implanted in the body for causing the drive mechanism to rotate the lead thereby to adjust the position of the at least one stimulating electrode on the lead relative to tissue in the body.

2. The method of claim 1 further including the step of:
  providing circuitry in the exterior signal generating and transmitting mechanism for sending a continuous signal or signal bursts to the signal receiving circuitry in the drive mechanism for causing continuous rotational movement or stepwise rotational movement of the lead.

3. The method of claim 1 wherein said at least one stimulating electrode is a spiral-shaped electrode.

4. The method of claim 1 including the step of:
  implanting a pulse generator in the body;
  electrically coupling the pulse generator to a proximal end of the drive mechanism; and,
  electrically coupling at least one signal channel of the pulse generator to one coupling electrode on a proximal end portion of the lead, whereby a stimulating signal from the pulse generator can be transmitted through the drive mechanism to the at least one stimulating electrode on the lead.

5. A system for non-invasively adjusting the position of at least one stimulating electrode on a lead implanted in a body relative to tissue in the body comprising:
  an implantable lead having at least one stimulating electrode thereon arranged skew to an elongate axis of the lead;
  an implantable drive mechanism having means for mechanically coupling to the implanted lead;
  means in said drive mechanism for causing rotation of said lead; and,
  signal receiving circuitry in said drive mechanism for receiving electromagnetic signals for causing actuation of said drive mechanism for rotating said lead.

6. The system of claim 5 wherein said means in said drive mechanism for causing rotation of said lead includes a micromotor.

7. The system of claim 5 wherein said means in said drive mechanism for causing rotation of said lead is mechanically coupled to a flexible, torqueable drive shaft in said implanted lead which is anchored to said implanted lead.

8. The system of claim 7 wherein said flexible, torqueable drive shaft is anchored to said implanted lead in a distal end portion thereof.

9. The system of claim 5 wherein said at least one electrode has a spiral configuration and is mounted in a spiral around a distal portion of said lead.

10. The system of claim 5 including an implantable pulse generator for generating stimulation signals.

11. The system of claim 10 wherein said implanted drive mechanism includes first electrical coupling means for electrically coupling at least one signal channel of said pulse generator to at least one conductor in said drive mechanism and second electrical coupling means for electrically coupling said at least one conductor to a proximal coupling electrode on a proximal end portion of said lead, said proximal coupling electrode being electrically coupled to said at least one stimulating electrode.

12. The system of claim 11 wherein said drive mechanism includes lead extension structure having mechanical coupling means for engaging and mechanically coupling with a proximal end or proximal end portion of said lead.

13. The system of claim 12 wherein said lead extension structure includes an elongate body having an opening at a distal end thereof for receiving said proximal end portion of said lead.

14. The system of claim 13 wherein said body has at least one electrode in said opening for electrically engaging with said at least one proximal coupling electrode on said proximal end portion of said lead.

15. The system of claim 14 wherein said at least one proximal coupling electrode is generally ring shaped.

16. The system of claim 15 wherein said one electrode in said opening comprises a garter spring shaped coil in said opening for frictionally engaging said generally ring shaped electrode.

17. The system of claim 5 including an exterior signal generating and transmitting mechanism for generating and transmitting electromagnetic signals from outside the body to said drive mechanism implanted in the body for causing said drive mechanism to rotate said lead thereby to adjust the position of said at least one stimulating electrode on said lead relative to tissue in the body.

18. The system of claim 17 including control circuitry in said exterior signal generating and transmitting mechanism for generating and sending a continuous signal or signal bursts to said signal receiving circuitry in said drive mechanism for causing continuous rotational movement or step-wise rotational movement of said lead.

19. The system of claim 17 wherein said drive mechanism includes a micromotor and said signal receiving circuitry includes an inductor for receiving signals from said exterior signal generating and transmitting mechanism, rectifying means coupled to said inductor and a capacitor coupled to an output of said rectifying means, said micromotor being connected to said capacitor.

20. The system of claim 17 wherein said control circuitry includes a DC power supply providing a supply voltage, a step-up DC-to-DC converter coupled to said power supply, a Colpitts oscillator coupled to an output of said DC-to-DC converter and an inductor coil/antenna coupled to an output of said Colpitts oscillator.

21. The system of claim 20 including pulse burst control circuitry coupled to an input of said Colpitts oscillator.

22. The system of claim 21 wherein said pulse burst control circuitry includes a bistable oscillator, pulse burst duration circuitry coupled to said bistable oscillator, switching circuitry for coupling through a NOR gate either said supply voltage or the output of said bistable oscillator to said Colpitts oscillator.

23. A method for non-invasively repositioning an electrode on a lead relative to nerve tissue in a body including the steps of:

providing a lead having at least one stimulating electrode thereon;

implanting the lead in a body;

implanting in the body a drive mechanism having structure for repositioning the at least one stimulating electrode relative to tissue in the body; and, providing an exterior signal generating and transmitting mechanism for transmitting electromagnetic signals from outside the body to the drive mechanism implanted in the body for causing the drive mechanism to reposition the at least one stimulating electrode relative to tissue in the body.

24. A system for non-invasively adjusting the position of at least one stimulating electrode on a lead implanted in a body relative to tissue in the body comprising:

an implantable lead having at least one stimulating electrode thereon;

an implantable drive mechanism having means for repositioning said at least one stimulating electrode relative to tissue in the body;

means in said drive mechanism for causing repositioning of said at least one stimulating electrode relative to tissue in the body; and, signal receiving circuitry in said drive mechanism for receiving electromagnetic signals for causing actuation of said drive mechanism for repositioning said at least one stimulating electrode.

25. The system of claim 24 including an exterior signal generating and transmitting mechanism for generating and transmitting electromagnetic signals from outside the body to said drive mechanism implanted in the body for causing said drive mechanism to reposition said stimulating electrode.

* * * * *